United States Patent [19]

Midgley et al.

[11] 4,366,143

[45] Dec. 28, 1982

[54] ASSAY FOR THE FREE PORTION OF SUBSTANCES IN BIOLOGICAL FLUIDS

[75] Inventors: John E. Midgley; Terence A. Wilkins, both of Amersham, Great Britain

[73] Assignee: Amersham International Public Limited Company, England

[21] Appl. No.: 189,942

[22] Filed: Sep. 22, 1980

[30] Foreign Application Priority Data

Sep. 24, 1979 [GB] United Kingdom ............... 7933072
Jan. 14, 1980 [GB] United Kingdom ............... 8001124

[51] Int. Cl.$^3$ ............................................ G01N 33/00
[52] U.S. Cl. ................................. 436/501; 436/503; 436/504; 424/1
[58] Field of Search ...................... 424/1, 12; 23/230 B

[56] References Cited

U.S. PATENT DOCUMENTS

| | | | |
|---|---|---|---|
| 4,046,870 | 9/1977 | Hertl et al. | 424/1 |
| 4,069,305 | 1/1978 | Polito et al. | 424/1 |
| 4,128,629 | 12/1978 | Eldred et al. | 424/1 |
| 4,225,574 | 9/1980 | Romelli et al. | 424/1 |
| 4,235,865 | 11/1980 | Thoma | 424/1 |

FOREIGN PATENT DOCUMENTS

| | | | |
|---|---|---|---|
| 2806860 | 9/1978 | Fed. Rep. of Germany | 424/1 |
| 2822462 | 12/1978 | Fed. Rep. of Germany | 424/1 |
| 2731028 | 1/1979 | Fed. Rep. of Germany | 424/1 |

OTHER PUBLICATIONS

Geokas et al., J. Biol. Chem., 1977, 252, 61–67.
Borgstrom et al., Scand. J. Clin. Labs. Invest., 1976, 36, 809–814.
Geokas et al., American Journal of Physiology, 1979, 236, Part 1, 77–83.

*Primary Examiner*—Christine M. Nucker
*Attorney, Agent, or Firm*—Wenderoth, Lind & Ponack

[57] ABSTRACT

A method of determining the concentration of the free portion of a ligand present in a biological fluid which also contains the ligand bound to one or more natural binders involves the single step of mixing a sample of the fluid with a labelled derivative of the ligand and a specific binder for the ligand, incubating the mixture, and determining the proportion of the labelled derivative of the ligand bound to the specific binder. The labelled derivative of the ligand is chosen to bind strongly to the added specific binder, but to bind not at all, or much more weakly than does the ligand, to the natural binders in the biological fluid. A small amount of the labelled derivative can be used, and the binding equilibrium of the ligand is not appreciably perturbed. Ligands include thyroxine, tri-iodothyroxine and cortisol.

16 Claims, 2 Drawing Figures

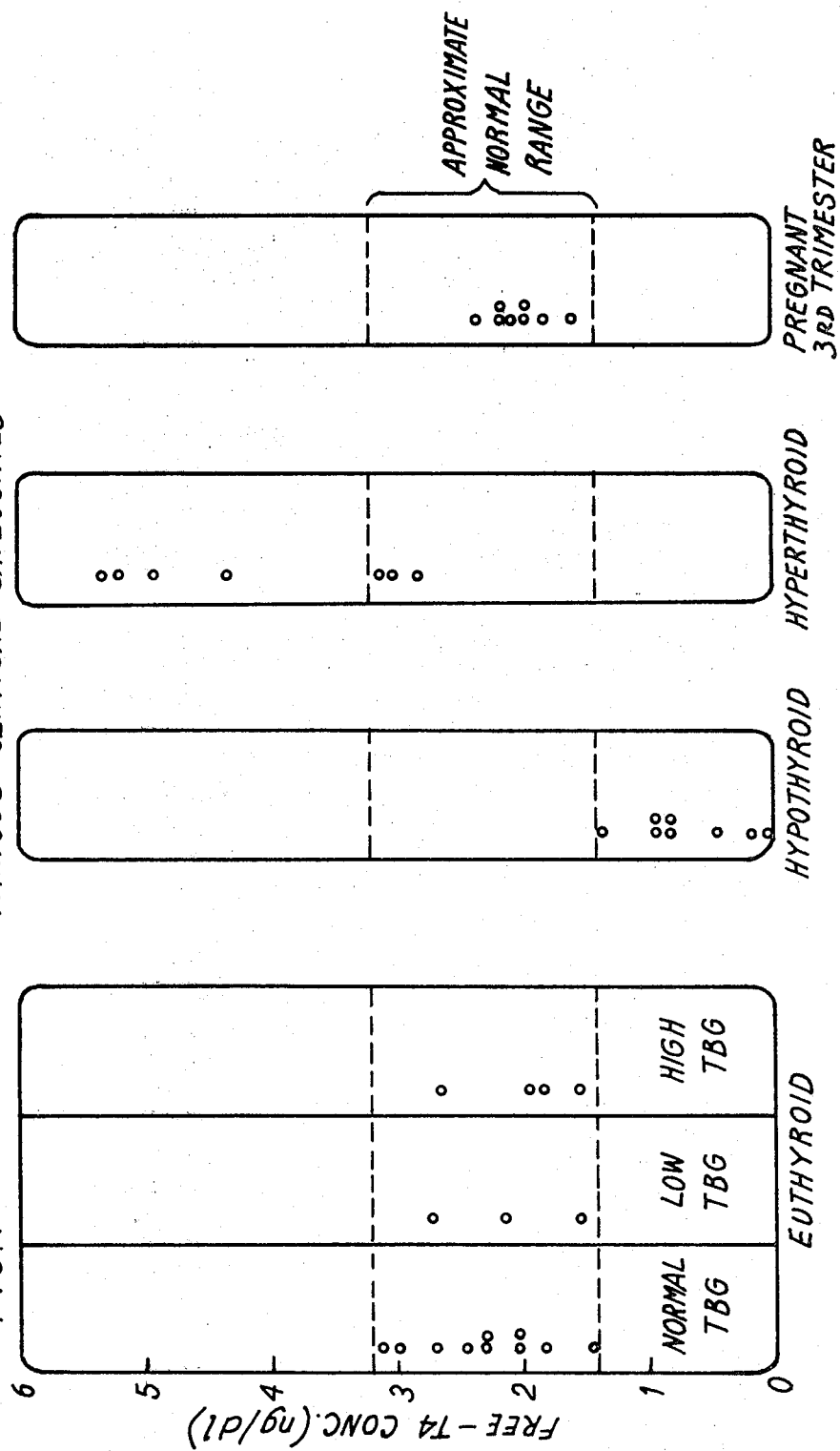

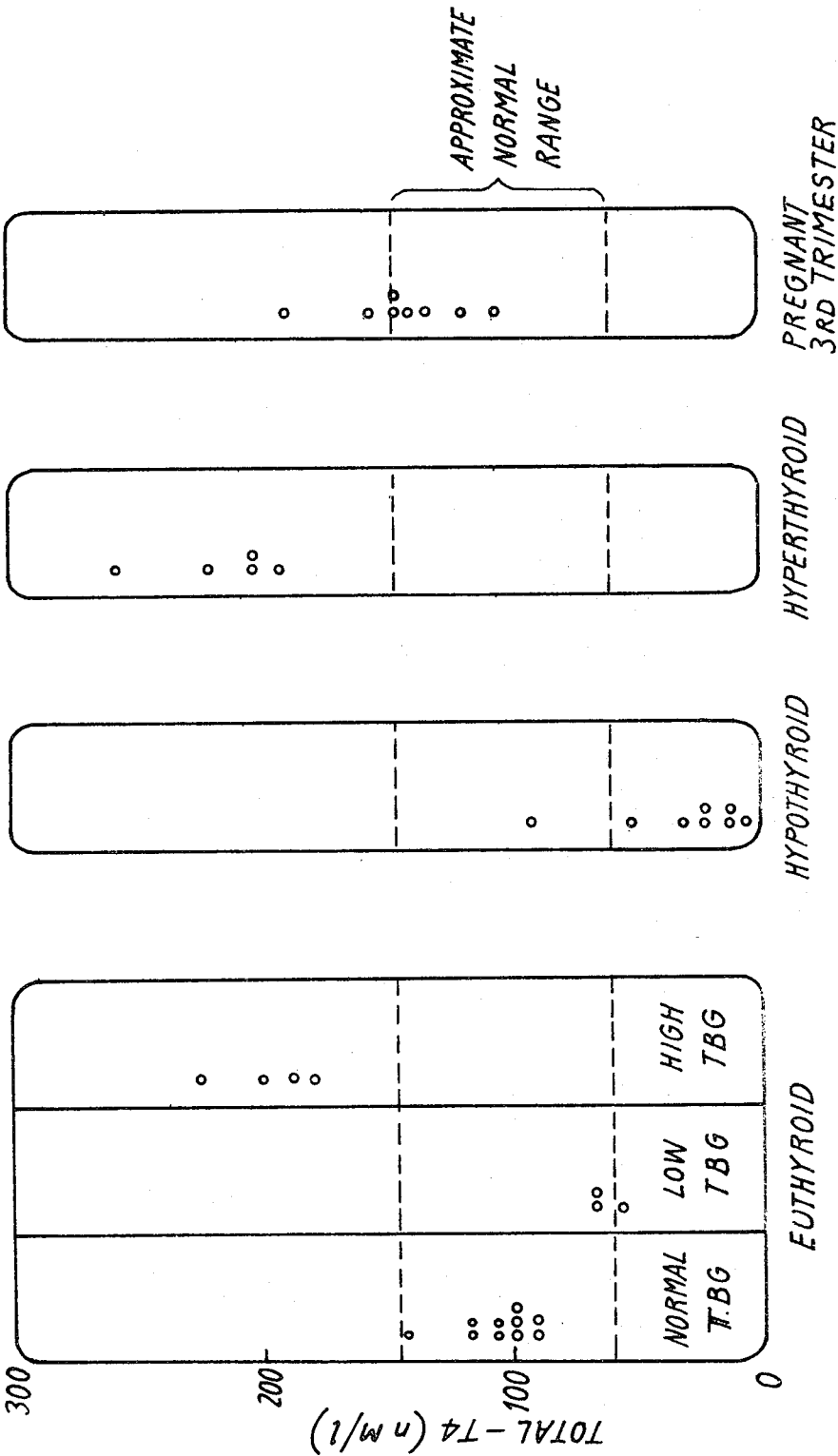

ASSAY FOR THE FREE PORTION OF SUBSTANCES IN BIOLOGICAL FLUIDS

This invention relates to an assay for the free portion of organic substances or ligands that are present in biological fluids in both a form bound to protein (or other binding species present in the fluid) and in a non-bound or free form. It relates to the field of competitive ligand binding assays: more specifically it relates to the field of immunoassays used to determine the concentration of a non-protein bound substance such as a hormone, a biochemical messenger, a steroid, a drug, a drug metabolite, a polypeptide or protein, a vitamin, a tumour antigen, a toxin, an alkaloid, a mono-, di- or polysaccharide in the presence of protein bound form(s) of that substance in a biological fluid such as blood plasma or serum.

For most physiologically active substances that can be found jointly in both a free form and a protein-bound form in biological fluids such as blood, it is currently thought that it is the concentration of the free form that may control the physiological responses associated with those substances and may therefore be more significant clinically than the concentration of total substance which includes both free (or unbound) and protein-bound substance.

A specific example of the importance of this general concept is illustrated by the role of thyroid hormones and their associated binding proteins in determining clinical status in thyroid disease. In the case of the thyroid hormones, (thyroxine and tri-iodothyronine), approximately 99.98% of thyroxine (T4) and 99.7% of tri-iodothyronine (T3) are bound to the naturally occurring binding proteins, thyroxine binding globulin (TBG), thyroxine binding pre-albumin (TBPA) and albumin (Alb) found in blood serum or plasma. Yet it is well known that the nature and often the severity of thyroid disease states may be better correlated with the free thyroid harmone concentration than with the total or protein-bound thyroid hormone concentration. Furthermore there are certain conditions, such as pregnancy or oestrogen drug therapy which significantly alter both the binding protein and the total thyroid hormone levels without any significant effect on free thyroid hormone concentration or thyroid clinical status.

A second example of the importance of the general concept is given by the role of the steroid hormone cortisol which is involved in the mechanism regulating the adrenal glands. Cortisol is found in blood plasma both in the free form (ca 8%) and also bound (ca 92%) to the naturally occurring plasma proteins transcortin and albumin. It is currently thought that it is the concentration of free (unbound) cortisol that regulates the pituitary in the feed-back mechanism of the adrenal-pituitary axis of healthy individuals. In a manner similar to thyroid hormone regulation, pregnancy causes significant increases in both cortisol and the major binding protein (transcortin) without causing any significant increase in adrenal-pituitary activity or free-cortisol concentrations. Similar arguments can be applied to the regulatory importance of free (unbound) portions of the steroid sex hormones, progesterone, testosterone and oestradiol in the gonadal-pituitary axis, where a high proportion (>90%) of the respective hormones are bound to plasma proteins such as sex hormone binding globulin and albumin.

The classical methods used at present for determining the free or unbound concentration of a substance in the presence of protein bound material involve the use of equilibrium dialysis. These methods, which are believed to give reasonably accurate estimates of the concentration of the free portion of most substances that are encountered in biological fluids in both the free and protein bound forms, are used for calibration purposes but are too slow, too tedious and too susceptible to experimental error for routine clinical use. In the field of thyroid hormone measurement alternative methods based largely on immunoassay techniques have been developed. In recent years, a number of kits which are alleged to measure free thyroxine concentrations have been placed on the market, as follows:

A. The Lepetit Kit. In this, the sample is absorbed into a column of Sephadex/buffer and incubated at 37° for one hour. The proteins are eluted with buffer. Free-T4 is eluted out with methanol into test tubes. The methanol is evaporated off and replaced by buffer. Solutions of T4 are then assayed by radioimmunoassay at 4° C. with an incubation period of 4 hours. This method is admitted by Lepetit to perturb the protein binding equilibria. The method is very tedious with very many operations required. Total assay time is about 1½ days and the precision is poor.

B. The Clinical Assays Kit. In this, the sample is incubated with buffer in an antibody-coated-tube at 37° C. for half an hour. The sample and buffer are removed and the tube washed.Tracer ($I^{125}$-labelled T4) and buffer are added, and the tube incubated at 37° C. for a further one hour. The tube is decanted, washed and counted.

In this kit there is competition between the antibody and the natural binding proteins for T4, and we interpret it as giving information related to the total amount of T4 in the system and the binding capacity of the natural binding proteins, and thus relating indirectly to the free T4, rather than giving a direct measure of free T4.

The kit has disadvantages of a very shallow dose-response curve and poor precision. The assay is prone to drift problems and therefore only a small number of unknowns can be assayed against a given set of standards. Total assay time is about 2½ hours.

C. The Damon Kit. In this, a solution containing a suspension of nylon microspheres encapsulating antiserum that has previously been equilibrated with tracer is pipetted into a tube with the sample. The tubes are incubated at 37° C. for one hour, vortexed and incubated for a further hour at 37° C. Extra buffer is added to each tube. These are then centrifuged, decanted and counted.

Dialysis and kinetic mechanisms have been advanced to explain the operation of this kit but, whatever its rationale, it suffers from very shallow dose-response and poor precision. In our hands, the results appeared to correlate better with total T4 than with free T4. Total assay time is about 3 hours.

D. The Pantex Kit. This is a two-assays-in-one kit. A separate RIA for total-T4 is carried out. This is followed by a T4-uptake test (i.e. a T3-uptake test wherein T3-$I^{125}$ has been substituted by T4-$I^{125}$). *The results of the T4-uptake test are calibrated in percent free-T4 values.* Free-T4 values are obtained by multiplying the results of the two tests together.

This kit has the disadvantage that two separate assays are required. The T4-uptake test very seriously perturbs the protein binding equilibria.

E. The Corning Kit. This is similar to the Pantex kit, except that Corning uses an antiserum, where Pantex uses Sephadex, to absorb unbound tracer in the T4-uptake test, and that the methods of calculation are somewhat different.

This kit has the disadvantage, like the Pantex kit, that two separate assays are required. It is acknowledged to be inaccurate for the TBG euthyroid patients. Also, it does not measure free T4, but some compromise between that and total T4.

British Patent Application No. 2,030,290 of Baxter Travenol Laboratories Inc. proposes a method for the determination of free analytes generally by contacting a sample containing the analyte in free and bound form with an unlabelled receptor to bind the free analyte, contacting the unlabelled receptor with a labelled analogue of the analyte, and measuring the proportion of label bound to the receptor.

This proposal has the disadvantage of requiring two steps.

There is a need for a method of asaying for the free portion of organic substances in biological fluids which avoids the disadvantages of the above-mentioned methods. The present invention aims to fulfil that need.

The present invention provides a method of determining the concentration of the free portion of a ligand present in a biological fluid which also contains a portion of the ligand bound to one or more natural binders, for the ligand, the bound and free portions of the ligand being in equilibrium with one another, by:

(a) admixing a sample of the fluid with a labelled derivative of the ligand and an added specific binder for the ligand whereby the free portion of the ligand and the labelled derivative thereof compete for reaction with the specific binder and become bound thereto in proportions which depend on the amount of the free ligand portion present in the sample, the respective amounts of said derivative and said specific binder being insufficient to substantially affect said equilibrium, and said labelled derivative being substantially non-reactive with said natural binders;

(b) effecting said reaction between the free ligand, the labelled derivative thereof and the specific binder;

(c) measuring the amount of the labelled derivative of the ligand, bound to the specific binder, and (d) using the said measurement to determine the concentration of free ligand in the biological fluid.

The ligand will generally be a hormone, a biochemical messenger, a steroid, a drug, a drug metabolite, a polypeptide or protein, a catecholamine, a vitamin, a tumour antigen, a toxin, an alkaloid, or a mono-, di-or polysaccharide.

The specific binder will generally be an antibody to the ligand to be measured or a reagent based upon such antibody or possibly a naturally occuring protein binder isolated from suitable biological materials.

The labelled derivative of the ligand has been chemically modified to inhibit its binding to the natural ligand binders, while retaining its ability to bind to the specific assay binder. Thus, the labelled derivative of the ligand should bind not at all, or much less strongly than does the ligand itself, to the natural ligand binders. Specifically, the affinity constant of the labelled derivative for each of the major naturally occuring binders should preferably be not more than 10% and ideally close to 0% of the affinity constant of the ligand for that natural binder. The binder strength of the labelled derivative of the ligand to the specific assay binder may suitably be comparable with the binding strength of the ligand to the specific assay binder; however, this comparison is not critical, and considerable variation can be tolerated while still giving an acceptable assay. It is essential that this labelled derivative of the ligand binds much less strongly (or not at all) to the natural ligand binders of the biological sample than to the added specific assay binder, though some binding of the labelled derivative of the ligand to minor weakly binding components of the natural ligand binders in the biological sample does not necessarily invalidate the method.

Because the labelled derivative does not significantly bind to the natural binding proteins, it is substantially all available for competition with the free ligand for reaction with the specific binder. It is in consequence possible to use a low concentration of specific binder while still obtaining a satisfactory dose-responsive curve. The use of a low concentration of specific binder is advantageous in that it does not lead to significant removal of ligand from the natural protein binders in the system.

At the same time, this derivative also contains or has linked to it a physical marker, such as a radioactive atom (or atoms) a fluorophor, a light chromophore, an enzyme or a chemiluminescent group. When radioactive labelling is used, Iodine-125 is a suitable isotope, but others will readily occur to those skilled in the art.

Separation of that portion of the ligand and labelled derivative thereof that has become bound to the specific binder, from that portion not so bound, may be effected by conventional means, such as chemical precipitation followed by centrifuging. Alternatively, it may be convenient to introduce the specific binder into the reaction medium on a solid support, such as for example, a polystyrene bead or a centrifugable polystyrene latex. Alternatively again, the specific binder may be provided in the form of a coating on the inner wall of the reaction vessel.

In certain techniques, where the label is for example an enzyme or a fluorescent molecule, it may not be necessary to separate bound from not-bound labelled ligand. Separation is necessary, however, when a radioactive label is used.

In a conventional radioimmunoassay the specific binder for the ligand (e.g. an antibody) is present in an amount insufficient to react with all of the ligand and its labelled version. At first sight, therefore, it might appear that, in the present invention, the specific binder must be present in an amount insufficient to react with all the free ligand and its labelled derivative. This is not so. Some of the labelled ligand derivative may be taken up on the natural ligand binders in the sample, and also, because some of the free ligand is removed by the specific binder, more ligand is removed from the natural binders to take its place. It may be advantageous, to employ an amount of specific binder greater than that required to react with all the free ligand initially present and its labelled derivative. Clearly an upper limit is set by that amount of specific binder which would react with all of the ligand present, whether free or bound to the natural binders, plus its labelled derivative, but this is not a very helpful indication for practical use.

It is to be recognised that at equilibrium the distribution of the labelled ligand derivative between the specific binder and elsewhere is determined by the amounts of natural and specific binders present, by their affinity constants for the ligand and its labelled derivative, and by the amounts of ligand and its labelled derivative present. While it might be theoretically possible to calculate the amount of ligand in the free form from a knowledge of the amount of labelled ligand derivative present on the specific binder and the other relevant data, this is not a practicable procedure, and recourse must be made to a standard procedure of radioimmunoassay, namely, the use of a "dose-response curve" or "standard curve". In this procedure, a number of standard sera, of known free ligand content (determined, for example, by equiibrium dialysis), spanning the required working range of the method, are measured in the procedure. The results are plotted graphically and unknown samples are read off against the curve. The actual amounts of sample, specific binder and labelled antigen derivative are optimized to give a dose response curve of adequate slope (and hence of adequate assay sensitents) over the desired working range of the assay. This process of optimizing an assay is one familiar to those who practice radioimmunoassay and related procedures.

However, there is a restriction upon the quantities of specific binder employed in the free ligand assay in that the greater the quantity employed, the more the position of equilibrium between free ligand and ligand bound to natural binder is altered; that is, the more the concentration of free liqand, at equilibrium, is altered. To some extent, the use of a dose response curve will correct for this, in that the position of equilibrium is altered in a similar way in the unknowns and in the standard samples. However, as the serum standards and the patient samples will inevitably have differing amounts of natural binders (it is the differing amounts of natural binders in different patient sera that render a free ligand assay valuable), it is highly desirable that the fraction of ligand removed from the natural binder (in terms of the total ligand present on the natural binder) should be as small as possible. This is a criterion which is readily met in cases such as T-4 and T-3 where the fraction present in the free form is very small. However, no general rules can be given in that the fraction of ligand which can permissibly be removed from the natural binder depends on the accuracy needed by the clinician in the particular test, the proportion of ligand normally present in the free state, the variability experienced in patient samples regarding concentrations of natural binders, and so on. It is, as it usually is in clinical radioimmunoassays, a matter of optimizing the assay for its intended purpose.

Arising out of this, it is preferred to use as small a quantity of specific binder as possible, consistent with obtaining a dose-response curve of adequate slope, so as to avoid perturbing the bound-free ligand equilibrium any more than is necessary.

By way of an example an assay, more specifically a radioimmunoassay, for the measurement of the free thyroxine concentration in serum has been developed using the principles described for this invention. Thyroxine (T4) is transported in the blood stream of human beings largely bound to the three naturally occuring T4-binding proteins TBG, TBPA and Albumin. The percentage of T4 bound to each of these is approximately 70%, 20-25% and 5-10% respectively. In synthesising a tracer for this particular assay it is important that the binding of the tracer to TBG and TBPA in the assay is zero or very much less than the binding of the tracer to the specific binder added in the assay. In this particular assay the binder requirements for the tracer with serum albumin are less stringent because only a small percentage of T4 is bound to albumin and the number of empty albumin binding sites is very large compared to the number of sites with T4 bound to them. This means that substantial quantities of tracer can be bound to serum albumin without displacement of any T4 that is bound.

With respect to the binding of T4 and derivatives thereof to TBG and TBPA, articles of interest include 'Thyroid Hormones and Analogs II Structure-Activity Relationships' by E. C. Jorgensen in "Hormonal Proteins and Peptides" Volume IV, Edited by C. H. Li, published by Academic Press, 1978, and references therein. From these it is clear that the binding of T4 to both TBG and TBPA is very dependent on the carboxylic acid and the amino group of the amino acid end of the T4 molecule. In the case of T4 derivatives that have had either or both of these groups removed or chemically modified to prevent them ionising in the usual way or modified by attachment of bulky chemical groups, the binding of the derivatives to TBG and TBPA is substantially reduced with respect to T4. On the other hand the binding strength of these derivatives with antisera raised to an immunogen consisting for example of a T4-methyl ester coupled via the amino groups to T4 to a large protein such as bovine serum albumin, is often comparable to that of T4 itself. Many other types of immunogen are suitable for use herein, and are known to those skilled in the art.

These properties may be achieved in the case of thyroxine (similar arguments can also be used for T3) by modifying the structure of T4 in one or more of the following ways:

1. Modifying the charge of the carboxylic acid and the terminal amino group of the alanine side chain of T4 or T3.
2. Adding a bulky group to either or both of the terminal carboxylic acid or amino groups.
3. Preparing derivatives of T4 or T3 with the D-configuration rather than the L-configuration.

The structure of the amino acid side chains is as follows:

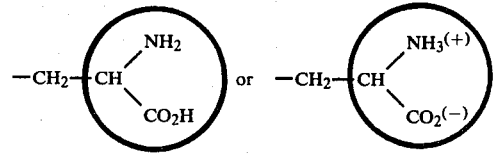

Modifications of types 1 and 2 can be summarised into carboxyl site (—COOH) and amino site (—NH2) modifications as follows:

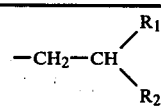

Possible carboxyl site modifications:-

| | | |
|---|---|---|
| (a) | R₁ = NH₂ | R₂ = H (Thyroxamine) |
| (b) | Esters | R₂ = CO₂Me, —CO₂Et, —CO₂Pr |
| (c) | Amides | R₂ = —CONH₂, CONHMe, CONHEt, —CON(Me)₂ |
| (d) | Peptides | R₂ = —CO(GLY), —CO(ALA) |
| (e) | Proteins | R₂ = —CO(BSA) |
| (f) | Amines | R₂ = —NH₂, —NHMe, —N(Me)₂, |
| (g) | Ketones | R₂ = —CO—CH₃ |

Possible amino site modifications:-

-continued $$-CH_2-CH\begin{matrix}R_1\\ \\R_2\end{matrix}$$

| | | |
|---|---|---|
| (a) | $R_2 = CO_2H$ | $R_1 = $ H (Thyroacetic Acid) |
| (b) | Amides | $R_1 = $ NHCOME, —NHCOEt |
| (c) | Peptides | $R_1 = $ —NH(GLY), —NH(ALA) |
| (d) | Proteins | $R_1 = $ —NH(BSA) |
| (e) | Amines | $R_1 = $ —NHMe, —N(Me)$_2$, —N(Me)$_3^{(+)}$ |

Clearly groups $R_1$ and $R_2$ could be replaced by other groups such as —CN, —OH, —CHO, —R (R=Alkyl or Aryl), —X (X=halide), —O—Me (Ether), organometallic, or metal chelate.

The use of D-Thyroxine derivatives may also be valuable. D-Thyroxine binds as strongly to antibodies as does the naturally occurring L-Thyroxine, while the binding of D-Thyroxine to TBG and TBPA is substantially less than that of L-Thyroxine.

By way of a second example, as assay more specifically a radioimmunoassay may be constructed for the measurement of the free cortisol concentration in plasma using the same principles as described above for the measurement of free thyroxine. Cortisol is transported in the blood stream of human beings largely bound to two naturally occurring binding proteins corticosteroid binding globulin (known also as CBG or transcortin) and serum albumin. Approximately 92% of the cortisol in healthy individuals is bound to these two plasma proteins, the greater proportions being bound to CBG. In synthesising a tracer for this particular assay it is important that the binding of the tracer to CBG is zero or very much less than the binding of the tracer to the specific binder added in the assay. In an analogous manner to the corresponding free-thyroxine assay, the binding requirements for the tracer with serum albumin are less stringent because only a small percentage of cortisol is believed to be bound to albumin and the number of empty albumin sites is very large compared to the number of sites with cortisol bound to them. This means that substantial quantities of tracer can be bound to serum albumin without displacement of any cortisol that is bound.

With respect to the binding of cortisol and derivatives thereof to CBG, articles of interest include:

(a) F. Le Guillard and M. Dantrevaux, *Biochimica et Biophysica Acta*, 495 (1977) p. 312–323.

(b) M. Basset, G. Defaye and E. M. Chambaz, *F.E.B.S. Letters*, 60, (1975) p. 365–368.

(c) M. K. Agarwal, *Arch. Biochem & Biophys*, 180 (1977), p. 140–145, and (d) A. A. Akhrem, A. A. Avvakumov, G. V. Kukushkina, I. I. Sviridov, O. V. Strelchenole, and O. A. Chashchim, *Vestsi. Akad Navuk, BSSR Ser. Khim. Navuk*, 2 (1978) p. 122–124.

From these it is clear that the binding of cortisol (and similarly progesterone) to CBG takes place through the A and B rings which it is believed fit into a cleft in the CBG molecule.

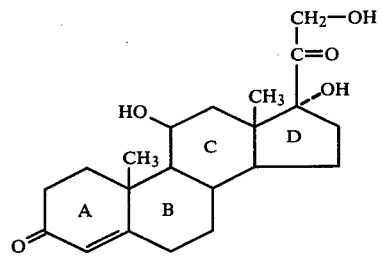

Substitution on the steroid nucleus with polar groups remote from the A and B rings appear to have little effect on the binding of the derivative to CBG, whereas the addition or substitution of suitable bulky or polar groups at or near the A and B rings appears to prevent binding of the derivatives to CBG.

With respect to the binding of cortisol and its derivatives to serum albumin, the U.S. Pat. No. 4,069,305, Jan. 17, 1978 (A. J. Pollito and W. S. Knight) is of interest, wherein it is reported that the derivative prepared by coupling the polar group histamine via a carboxymethyloxime bridge to the 3 position of the A ring of cortisol, binds much less strongly to serum albumin than cortisol itself.

Antisera specific to cortisol are raised to an immunogen consisting of cortisol coupled via an aliphatic bridge to a large protein such as bovine serum albumin. Whilst in principle the bridging group could be attached to almost any of the carbon atoms of the steroid molecule, the 3-, 6- and 21-positions are most favoured for reasons of convenience and specificity. With the possible exception of H-3 labelled cortisol, tracers for cortisol immunoassays are synthesised by linking a marker group via an aliphatic bridge to the steroid molecule. The marker group may be histamine or tyrosine-methyl-ester moieties which when linked to the steroid may be labelled with I-125. Alternatively the marker group may be an enzyme, a fluorophore, a light chromophore or a chemi-luminescent group. It is convenient to combine the need to link a marker group to the steroid with the need to inhibit CBG and albumin binding of the tracer by linking a group which is bulky, polar and acts as a physical marker via an aliphatic bridge to the A or B rings of the steroid nucleus preferably at the 3- or 6-positions. A tracer synthesised in this way will exhibit zero or very low binding to CBG and albumin with respect to cortisol.

By way of an example, suitable tracers for a free-cortisol assay may be synthesised by:

(1) Coupling histamine or tyrosine derivatives to the 3- or 6-positions via a bridge consisting of either an O-carboxy-methyl-oxime group, or a carboxyethylthio-ether group, or a hemi-succinate, or a hemi-fumarate or a hemi-adipate or a hemi-glutarate or a hemi-phthalate.

(2) Radiolabelling the so attached marker group with I-125.

It is important that tracers synthesised in this way bind strongly to specific cortisol antisera as well as having little or no binding with CBG and albumin. This property may most readily be achieved by using an antiserum raised to immunogen which is structurally homologous with the tracer. By way of an example, a suitable antiserum for a histamine-3-carboxymethyloxime-cortisol-I-125 tracer would be obtained by using a bovine serum albumin-3-carboxymethyloxime-cortisol immunogen to raise the antibodies. It is not however essential to use a matched homologous tracer-immunogen pair. In some cases a heterologous tracer-immunogen pair may be used. By way of an example an antiserum raised to a 21-hemisuccinate-cortisol conjugate to bovine serum albumin possesses sufficient affinity for a histamine-3-carboxymethyloxime-cortisol-I-125 tracer to enable it to be used in a free cortisol radioimmunoassay.

The principles described for the assay of free cortisol apply also to the steroids progesterone, oestradiol and testosterone. It is well known that progesterone binds to CBG through its A and B rings in the same manner as cortisol. Similarly the sex hormones testosterone and oestradiol bind strongly to the protein sex hormone binding globulin (SHBG) and this binding is believed to be through the A and B rings. Articles of interest here are:

(a) C. Bonne and J. Raymond, Steroids, 27 (1976) p. 497–507.
(b) D. Philibert and J. P. Raymond, Endocrinol, 94, (1974) p. 627.
(c) J. P. Raymond, Steroids, 21 (1973) p. 249.

The following Examples illustrate the invention.

EXAMPLE 1

Free T4 Assay

The labelled derivative of the ligand was N-acetyl-thyroxine-methyl ester, labelled by iodine-125 exchange using sodium iodide-$I^{125}$ and chloramine-T. The specific activity was 1500 millicuries per milligram. The tractor concentration was 90 picomolar.

The specific binder was a solution of sheep-anti-T4 serum raised against thyroxine methyl ester coupled to bovine serum albumin by carbodiimide. The final dilution was 1/60,000 in buffer.

The buffer contained 13.6 g/l $KH_2PO_4$, 9.0 g/l NaCl, 0.07 g/l $NaN_3$ and 1.0 g/l gelatin.

50 micro-liters of a serum sample was mixed with 200 micro-liters of the radioactive ligand derivative solution and 200 micro-liters of specific binder solution and the mixture incubated at room temperature for one hour. Then 1 milli-liter of polyethyleneglycol solution (20%) was added, and the reaction mixture centrifuged. The supernatant liquid was decanted and the radioactivity of the precipitate was measured.

The following results were typical of those obtained by this technique.

| Free T4 (ng/dl) | % Radioactivity in Solid Phase |
| --- | --- |
| 0.0 | 58 |
| 0.2 | 55 |
| 1.0 | 47 |
| 3.0 | 34 |
| 5.8 | 22 |

EXAMPLE 2

Some preliminary clinical data has been obtained, and the results are set out in FIGS. 1 and 2, in which each spot represents a patient. FIG. 1 shows free-T4 concentrations for samples from patients in various clinical categories, measured by the method of this invention. FIG. 2 shows total-T4 concentrations for samples from the same patients measured by conventional means. It should be noted that the free-T4 values for pregnant women and euthyroid patients with high or low levels of thyroxine binding globulin all fall, as they should, within the normal range.

EXAMPLE 3

Dilution Experiment

When samples are diluted with water or buffer and then assayed in a total-T4 RIA the measured total-T4 values decrease in proportion to the dilution of the sample.

It has been demonstrated theoretically by Oppenheimer and Surks (J. H. H. Oppenheimer and M. I. Surks, J. Clin. Endocrinology and Metabolism, 24, pp. 785–793, (1964) that the free-T4 concentration of human serum samples is unaffected by dilution within certain limits.

Thus with genuine free-T4 assays it is possible to dilute serum samples and yet not greatly affect the measured free-T4 concentration.

To test the assay of this invention in this respect, an euthyroid sample has been diluted in the same buffer as used in the assay. The results were as follows:

| Dilution | Expected Total-T4 (μg/dl) | Measured Free-T4 (ng/dl) |
| --- | --- | --- |
| None | 7.3 | 2.3 |
| 1:2 | 3.7 | 2.0 |
| 1:5 | 1.5 | 1.9 |
| 1:10 | 0.7 | 2.7 |

EXAMPLE 4

This experiment is designed to compare the binding of cortisol-3-carboxymethyloxime-histamine $I^{125}$ to transcortin with that or cortisol itself. The protocol was as follows:

A. 100 μl charcoal extracted human serum (containing 0.01 μCi of either Cortisol ($H^3$) tracer or cortisol-3-carboxymethyloxime-histamine $I^{125}$ tracer).

B. 200 μl buffer (containing either 0 or 600 μg of 8-anilinonaphthalene sulphonic acid (ANS) as a cortisol binding site blocking agent).

A mixture of A and B was incubated at 37° C. for one hour. Resin (1 ml of a buffered suspension of Biorad AG 1-X2 anion-exchange resin (200–400 mesh) chloride form 15% w/v) was then added. The reaction tubes were mixed for one hour at room temperature. A 0.5 ml aliquot of the supernatant was then removed for counting.

The results were as follows:

| | % Tracer Bound to Serum Proteins (Corrected for Non-Specific Binding) | |
| --- | --- | --- |
| | ANS Concentration (μg/tube) | |
| Tracer | 0 | 600 |
| Cortisol ($H^3$) | 28 | 3.5 |
| Cortisol-3-carboxymethyl-oxime-histamine $I^{125}$ | 7 | 5 |

The ($H^3$) tracer binds strongly to transcortin, but is displaced at high concentrations of the ANS blocking agent. The 3-CMO-histamine $I^{125}$ tracer binds very weakly to transcortin, and is not significantly displaced by the ANS blocking agent, which suggests that the binding involved is different in character from that between cortisol and transcortin.

EXAMPLE 5

This experiment is designed to test the binding of cortisol-3-carboxymethyl oxime-histamine-$I^{125}$ tracer with an antiserum raised to a cortisol-3-carboxymethyloxime-thyroglobulin conjugate. The protocol was as follows:

50 μl of serum was mixed with 200 μl of cortisol-3-carboxymethyloxime-histamine-$I^{125}$ tracer solution. The specific activity of the tracer was 3.9 curies per milligram. The tracer concentration was 125 picomolar. The buffer contained 28 g/l $Na_2HPO_4.12H_2O$, 4.6 g/l citric acid monohydrate, 9 g/l NaCl, 3 g/l E.D.T.A. disodium salt, 0.5 g/l $NaN_3$, 1 g/l gelatin and 1 g/l of 8-anilinonaphthalene sulphonic acid (the latter to inhibit binding of cortisol to transcortin and albumin).

To the mixture of tracer and serum, 200 μl of a suspension of polystyrene latex particles (0.9 micron diameter) coated with the rabbit anti-cortisol serum was added. The buffer was 28 g/l $Na_2HPO_4.12H_2O$, 4.6 g/l citric acid monohydrate, 0.5 g/l $NaN_3$ and 2 g/l bovine serum albumin. The effective antiserum dilution in the assay tube was 1/20000.

The resulting mixture was vortexed and incubated at 37° C. for 1 hour. The antibody coated particles were centrifuged down at 1500 g for 15 minutes and the liquid phase decanted off.

The following results were typical of those obtained by this technique:

| Total Plasma Cortisol (μg/dl) | % Radioactivity in the anitbody Coated Particles |
| --- | --- |
| 0 | 65.4 |
| 1 | 56.6 |
| 4 | 43.0 |
| 10 | 30.6 |
| 28 | 19.2 |
| 60 | 12.2 |

EXAMPLE 6

Free T4 Assay using N-acetyl-thyroxine-dimethylamide

The labelled derivative of the ligand was N-acetyl-thyroxine-dimethylamide, labelled by iodine-125 exchange using sodium iodide $I^{125}$ and chloromine-T. The specific activity was 1000 millicuries per milligram. The tracer concentration was 0.5 μCi/ml.

The specific binder was a pre-precipitated double antibody complex made from sheep anti-T4 serum and donkey anti-rabbit γ globulin serum. This reagent is referred to as the T4-binding reagent.

The buffer was 0.01 molar phosphate, pH 7.4, containing 9.0 g/l NaCl, 1.0 g/l $NaN_3$ and 1.0 g/l gelatin. 50 micro-liters of a serum sample or standard was mixed with 500 micro-liters of the tracer solution and 1000 micro-liters of the T4-binding reagent. The mixture was incubated for 2 hours at 37° C., centrifuged, decanted, and drained. The radioactivity of the precipitate was measured.

The following results are the mean of those obtained on duplicate tubes.

| Free T4 (ng/dl) | % Radioactivity in Solid Phase |
| --- | --- |
| 0 | 38 |
| 0.18 | 22 |
| 0.9 | 11 |
| 3.0 | 6.0 |
| 5.7 | 3.6 |

A non-pregnant euthyroid control gave a figure of 7.1%, indicating a free thyroxine concentration of 1.8 ng/dl.

A pregnant euthyroid control gave a figure of 6.8%, indicating a free thyroxine concentration of 2.0 ng/dl.

Use of the assay of this Example on the sera of a total of 55 patients gave results, expressed as free T4 concentration in ng/dl, as follows:

| | | |
| --- | --- | --- |
| Hypothyroid (10 patients) | range 0.2–1.2 | mean 0.78 |
| Hyperthyroid (8 patients) | range 2.7–4.5 | mean 3.5 |
| Euthyroid (11 patients) | range 0.9–1.8 | mean 1.47 |
| Pregnant euthyroid (9 patients) | range 1.4–2.4 | mean 1.87 |
| Low TBG euthyroid (13 patients) | range 0.8–2.1 | mean 1.18 |
| Low TBG euthyroid on drugs (4 patients) | range 0.8–1.9 | mean 1.24 |

Figures obtained in this survey were compared to figures for free thyroxine index (FTI) obtained by conventional means on the same patients. The correlation coefficient was 0.94.

EXAMPLE 7

List of T4 derivatives prepared and iodinated for testing in the free T4 assay system D-T4
L-T4/A (N-Acetyl-L-T4-methylester)
D-T4/A (N-Acetyl D-T4-methylester)
L-T4/F (N-Acetyl-L-T4)
L-T4/L (N-Acetyl-L-T4-monoethylamide)
L-T4/M (N-Acetyl-L-T4-dimethylamide)

Method of testing for binding of T4 derivatives to TBG

The dominant binding protein for T4 in serum is TBG, and the binding site for T4 on this protein may be blocked by adding an appropriate concentration of thiomersalate to the buffer. Hence it is possible to obtain a good indication of the binding of a T4 derivative to TBG by comparing the binding to antiserum in the presence and absence of the blocking agent.

The labelled T4 derivative was dissolved in 0.01 molar phosphate, pH 7.4 containing 0.9% sodium chloride and 0.1% gelatin to give a radioactive concentration of approximately 0.05 microcuries per milliliter. In the part of the experiment where the blocking agent was used, this buffer contained 1.8% thiomersal.

A solid phase T4 specific antibody was used that consisted of a pre-precipitated double antibody complex made by reacting sheep anti-T4 serum and donkey antirabbit gamma globulin serum in the abovementioned phosphate buffer. A concentration of this solid phase T4 antibody suspension was chosen that bound approximately 50% of $^{125}I$-T4 tracer in the presence of blocking agent under the experimental conditions used.

The binding of the labelled T4 derivatives was tested as follows:

50 µl human serum (depleted of T4 by resin extraction)

500 µl labelled T4 derivative (with or without blocking agent)

1.0 ml solid phase T4 antibody suspension

Tubes were incubated for 2 hours at 37° C. and then centrifuged to settle the solid phase antibody. The supernatant solution was decanted and the radioactivity in the solid phase measured.

Using this technique the following results were typically obtained:

| $^{125}$I-labelled T4 derivative | % of T4 derivative bound to antibody | | Ratio |
|---|---|---|---|
| | Thiomersal absent | Thiomersal present | |
| L - T4 | 12 | 50 | 0.24 |
| D - T4 | 24 | 50 | 0.48 |
| L - T4/L | 21 | 60 | 0.35 |
| L - T4/F | 22 | 52 | 0.42 |
| L - T4/A | 36 | 40 | 0.90 |
| D - T4/A | 38 | 38 | 1.00 |
| L - T4/M | 50 | 50 | 1.00 |

It is seen that L-T4 is bound appreciably by TBG, because less is bound to the antibody in the absence, rather than in the presence of blocking agent. D-T4, however is bound less by TBG. Both of these results are as would be expected.

L-T4/L and L-T4/F are both bound to TBG to about the same extent as D-T4. L-T4/A appears to bind much less strongly to TBG than does L-T4 because the binding to antibody in the presence and absence of blocking agent is almost the same. Use of the D-isomer of T4/A appears to decrease this binding to TBG even further as the binding of D-T4/A to antibody is apparently unaffected by the presence or absence of blocking agent. Similarly, L-T4/M appears to have minimal binding to TBG.

This demonstrates that it is possible to modify the side chain of thyroxine to inhibit its binding to TBG and that the use of the D isomer of a T4 derivative can be advantageous in this respect. While D-T4, L-T4/L and L-T4/F have reduced binding to TBG, this is not reduced enough for consideration as a T4 derivative for a free-T4 assay. L-T4/A, D-T4/A and L-T4/M, however have sufficiently reduced binding to TBG for use in the free-T4 assay.

The right-hand column of the above table sets out the ratio of the figures in the two other columns. As a rule of thumb, it may be said that this ratio should be at least 0.6, preferably at least 0.9 for the compound tested to be worth considering for use in the free T4 assay. It should be noted, however, that these figures are valid only for the free T4 assay and not necessarily for other free ligand assays.

We claim:

1. A method of determining the concentration of the free portion of a ligand present in a biological fluid which also contains a portion of the ligand bound to one or more natural binders for the ligand, the bound and free portions of the ligand being in equilibrium with one another, by:

(a) admixing a sample of the biological fluid with an amount of a labelled derivative of the ligand and an amount of an added specific binder for the ligand whereby the free portion of the ligand and the labelled derivative thereof compete for reaction with the specific binder and become bound thereto in proportions which depend on the amount of the free ligand portion present in the sample, the respective amounts of said derivative and said specific binder being insufficient to substantially affect said equilibrium and said labelled derivative being substantially non-reactive with said natural binders;

(b) effecting said reaction between the free ligand, the labelled derivative thereof and the specific binder;

(c) measuring the amount of the labelled derivative of the ligand bound to the specific binder; and (d) using the measurement to determine the concentration of free ligand in the biological fluid.

2. A method as claimed in claim 1, wherein the ligand is a hormone, a biochemical messenger, a steroid, a drug, a drug metabolite, a polypeptide, a protein, a catecholamine, a vitamin, a tumour antigen, a toxin, an alkaloid or a mono-, di- or polysaccharide.

3. A method as claimed in claim 2, wherein the ligand is a thyroid hormone, cortisol, progesterone, oestradiol or testosterone.

4. A method as claimed in claim 1 wherein the specific binder is an antibody to the ligand or a reagent based upon such antibody.

5. A method as claimed in claim 1 wherein the labelled derivative of the ligand has linked to it a radioactive atom or atoms, a fluorophor, a light chromophore, an enzyme or a chemiluminescent group.

6. A method as claimed in claim 1 wherein the ligand is (T4) or tri-iodothyronine (T3), and the labelled derivative of the ligand is a derivative of thyroxine or tri-iodothyronine which has been modified at one or both of the carboxyl group and the amino group.

7. A method as claimed in claim 6, wherein the said modification of T4 or T3 has been effected in one or more of the following ways:-

(a) modifying the charge of the carboxylic acid and the terminal amino group of the alanine side chain of T4 or T3;

(b) adding a bulky group to either or both of the terminal carboxylic acid or amino groups;

(c) preparing derivatives of T4 or T3 with the D-configuration rather than with the L-configuration.

8. A method as claimed in claim 7, wherein the labelled derivative of the ligand is selected from the N-acetyl-methylester and the N-acetyl-dimethylamide of D-T3, L-T3, D-T4 or L-T4 which has been labelled with iodine-125.

9. A method as claimed in claim 1 wherein the ligand is selected from cortisol, progesterone, oestradiol and testosterone, and the labelled derivative of the ligand has been modified by the addition or substitution of at least one bulky or polar group at or near the A or B ring thereof.

10. A method of determining the concentration of the free portion of a ligand present in a biological fluid which also contains a portion of the ligand bound to one or more natural binders for the ligand, the bound and free portions of the ligand being in equilibrium with one another, by:

(a) admixing a sample of the biological fluid, with an amount of a labelled derivative of the ligand and an amount of an added specific binder for the ligand whereby the free portion of the ligand and the labelled derivative thereof compete for reaction with the specific binder and become bound thereto in proportions which depend on the amount of the free ligand portion present in the sample, the respective amounts of said derivative and said specific binder being insufficient to substantially affect said equilibrium, and said labelled derivative being substantially non-reactive with said natural binders;

(b) effecting said reaction between the free ligand, the labelled derivative thereof and the specific binder;

(c) separating that portion of the ligand and the labelled derivative thereof that has become bound to the specific binder from the portion of ligand and derivative therof not bound to the specific binder;

(d) measuring the amount of the labelled derivative of the ligand bound to the specific binder; and, (e) using the measurement to determine the concentration of free ligand in the biological fluid.

11. A method as claimed in claim 1 or 10, wherein the concentration of the chosen specific binder is relatively low consistent with obtaining a dose-response curve of adequate slope over the desired working range of the assay and avoiding substantially perturbing the bound-free ligand equilibrium.

12. A method as claimed in claim 1 wherein step (d) is performed by generating a standard curve of measured labelled derivative concentration against free ligand concentration of standard biological samples of known free ligand content, and checking the said measurement of step (c) against the said standard curve.

13. The method in accordance with claim 1 or 10 wherein the specific binder is introduced to the reaction medium on a solid support.

14. The method in accordance with claim 1 or 10 wherein the specific binder is provided in the form of a coating on the inner wall of a reaction vessel.

15. The method in accordance with claim 10 wherein the labelled derivative is radioactivety labelled.

16. The method in accordance with claim 6 wherein said reaction is effected for about one-two hours at about 37° C.

* * * * *